United States Patent [19]

Malloy et al.

[11] Patent Number: 4,581,336

[45] Date of Patent: Apr. 8, 1986

[54] SURFACE-MODIFIED ELECTRODES

[75] Inventors: Thomas P. Malloy, Lake Zurich; Louis J. DeFilippi, Mount Prospect, both of Ill.

[73] Assignee: UOP Inc., Des Plaines, Ill.

[21] Appl. No.: 539,195

[22] Filed: Oct. 5, 1983

Related U.S. Application Data

[63] Continuation-in-part of Ser. No. 371,703, Apr. 26, 1982, abandoned.

[51] Int. Cl.$^4$ .................. C12N 11/14; C12N 11/08; C12N 11/06; C12M 1/40
[52] U.S. Cl. ................................. 435/176; 204/403; 435/180; 435/181; 435/288
[58] Field of Search ............... 435/176, 180, 181, 288; 204/403

[56] References Cited

U.S. PATENT DOCUMENTS

| | | | |
|---|---|---|---|
| 3,651,386 | 3/1972 | Youtsey et al. | 357/10 |
| 4,229,536 | 10/1980 | DeFilippi | 435/176 |
| 4,240,889 | 12/1980 | Yoda et al. | 435/288 X |
| 4,307,195 | 12/1981 | Karasama et al. | 435/288 |
| 4,321,123 | 3/1982 | Nakamura et al. | 435/288 |

Primary Examiner—David M. Naff

Attorney, Agent, or Firm—Thomas K. McBride; William H. Page, II; Raymond H. Nelson

[57] ABSTRACT

Surface-modified electrodes which may be used in electrochemical cells for production of electrical energy comprise an enzyme immobilized on a support. The support consists of at least a monolayer coating of a carbonaceous pyropolymer possessing recurring units containing at least carbon and hydrogen atoms composited on a high surface area refractory inorganic oxide such that the carbonaceous pyropolymer monolayer coating replicates the surface area and macropore volume of the inorganic oxide. The coated support is then treated by impregnation with a water-soluble polyamine followed by contact with a solution of a molar excess of a bifunctional monomeric material to form a copolymer which provides pendant bonding sites. The copolymer is entrapped and adsorbed in the pores of the support material to provide a permanent attachment thereto. The treated support is then contacted with an excess of an enzyme to effect the conjugate attachment of the enzyme to the treated support. The immobilized enzyme will act as a working electrode in the presence of a predetermined substrate such as glucose to provide electrical energy.

22 Claims, No Drawings

SURFACE-MODIFIED ELECTRODES

CROSS-REFERENCE TO RELATED APPLICATION

This application is a continuation-in-part of our co-pending application Ser. No. 371,703 filed April 26, 1982, now abandoned, all teachings of which are incorporated herein by reference thereto.

BACKGROUND OF THE INVENTION

Enzymes, which are proteinaceous in nature and which are commonly water-soluble, comprise biological catalysts which may serve to regulate many and varied catalytic reactions. The use of enzymes in analytical, medical and industrial applications are well known. For example, enzymes find use in industrial applications, in the preparation of food products such as cheese or bread, in the resolution of amino acids, in the modification of penicillin to form various substrates thereof, etc. These uses, as well as many others, have been well delineated in the literature.

In addition, enzymes have also been used in conjunction with electrodes in biochemical fuel cells for a wide variety of purposes. In this respect, the soluble enzymes such as glucose oxidase along with iron powder on a glass stirrer and a platinum electrode constitute one variation of a biofuel cell which generates currents in the range of low microamps. Another type of biofuel cell modified the aforementioned arrangement by including a redox intermediate to accept electrons from the enzyme and transfer them to the anodic electrode. As in the previous arrangement, soluble enzymes were used and currents of relatively low milliamps were obtained.

As hereinbefore set forth, inasmuch as enzymes are commonly water-soluble as well as being generally unstable and readily deactivated they are also difficult either to remove from the solutions in which they are utilized for subsequent reuse or it is difficult to maintain their catalytic activity for a relatively extended period of time. The aforementioned difficulties will, of course, lead to an increase cost in the use of enzymes for commercial purposes due to the necessity for frequent replacement of the enzyme, this replacement being usually necessary with each application. To counteract the high cost of replacement, it has been suggested to immobilize or insolubilize the enzymes prior to the use thereof. By immobilizing the enzymes through various systems hereinafter set forth in greater detail, it is possible to stabilize the enzymes in a relative manner and, therefore, to permit the reuse of the enzyme which may otherwise undergo deactivation or be lost in the reaction medium. Such immobilized or insolubilized enzymes may be employed in various reactor systems such as in packed columns, stirred tank reactors, etc., depending upon the nature of the substrate which is utilized therein. In general, the immobilization of the enzymes provides a more favorable or broader environmental and structural stability, a minimum of effluent problems and materials handling as well as the possibility of upgrading the activity of the enzyme itself.

For example, in recent times enzymes have been immobilized in a biofuel cell adjacent to the electrode surface. Glucose oxidase has been immobilized on a platinum surface by encasement in an acrylamide gel matrix, thereby facilitating the reuse of the enzyme.

As hereinbefore set forth, several general methods, as well as many modifications thereof, have been described by which the immobilization of enzymes may be effected. One general method is to adsorb the enzyme on a solid surface as, for example, when an enzyme such as amino acid acylase is adsorbed on a cellulosic derivative such as DEAE-cellulose; papain or ribonuclease is adsorbed on porous glass; catalase is adsorbed on charcoal; trypsin is adsorbed on quartz glass or cellulose, chymotrypsin is adsorbed on kaolinite, etc. Another general method is to trap an enzyme in a gel lattice such as glucose oxidase, urease, papain, etc., being entrapped in a polyacrylamide gel; acetyl cholinesterase being entrapped in a starch gel or a silicone polymer; glutamic-pyruvic transamiase being entrapped in a polyamide or cellulose acetate gel, etc. A further general method is a cross-linking by means of bifunctional reagents and may be effected in combination with either of the aforementioned general methods of immobilization. When utilizing this method, bifunctional or polyfunctional reagents which may induce intermolecular cross-linking will covalently bind the enzymes to each other as well as on a solid support. This method may be exemplified by the use of glutaraldehyde or bisdiazobenzidine-2,2'-disulfonic acid to bind an enzyme such as papain on a solid support, etc. A still further method of immobilizing an enzyme comprises the method of a covalent binding in which enzymes such as glucoamylase, trypsin, papain, pronase, amylase, glucose oxidase, pepsin, rennin, fungal protease, lactase, etc., are immobilized by covalent attachment to a polymeric material which is attached by various means to an organic or inorganic solid porous support. This method may also be combined with the aforesaid immobilization procedures.

The above enumerated methods of immobilizing enzymes all possess some drawbacks which detract from their use in industrial processes. For example, when an enzyme is directly adsorbed on the surface of a support, the binding forces which result between the enzyme and the carrier support are often quite weak, although some prior art has indicated that relatively stable conjugates of this type have been obtained when the pore size of the support and the spin diameter of the enzyme are correlated. However, in such cases it is specified that the pore size of the support cannot exceed a diameter of about 1,000 Angstroms. In view of this weak bond, the enzyme is often readily desorbed in the presence of solutions of the substrate being processed. In addition to this, the enzyme may be partially or extensively deactivated due to its lack of mobility or due to interaction between the support and the active site of the enzyme. Another process which may be employed is the entrapment of enzymes in gel lattices which can be effected by polymerizing an aqueous solution or emulsion containing the monomeric form of the polymer and the enzyme or by incorporating the enzyme into the preformed polymer by various techniques, often in the presence of a cross-linking agent. While this method of immobilizing enzymes has an advantage in that the reaction conditions utilized to effect the entrapment are usually mild so that often there is little alteration or deactivation of the enzyme, it also has disadvantages in that the conjugate has poor mechanical strength, which results in compacting when used in columns in continuous flow systems, with a concomitant plugging of the column. Such systems also have rather wide variations in pore size, thus leading to some pore sizes which are large enough to permit the loss of enzyme. In addition, some pore sizes may be sufficiently small so that large diffusional barriers to the transport of the substrate and product will lead to reaction retardation, this being especially true when using a high molecular weight substrate. The disadvantages which are present when immobilizing an enzyme by intermolecular cross-linkage, as already noted, are due to the lack of mobility with resulting deactivation because of inability of the enzyme to assume the natural configuration necessary for maximum activity, particularly when the active site is involved in the binding process.

Covalent binding methods have found wide applications and may be used either as the sole immobilization technique or as an integral part of many of the methods already described in which cross-linking reactions are employed. This method is often used to bind the enzyme as well as the support through a bifunctional intermediary molecule in which the functional groups of the molecule, such as, for example, gamma-aminopropyltriethoxysilane, are capable of reacting with functional moieties present in both the enzyme and either an organic or inorganic porous support. A wide variety of reagents and supports has been employed in this manner and the method has the advantage of providing strong covalent bonds throughout the conjugate product as well as great activity in many cases. The covalent linkage of the enzyme to the carrier must be accomplished through functional groups on the enzyme which are non-essential for its catalytic activity such as certain free amino groups, carboxyl groups, hydroxyl groups, phenolic groups, sulfhydryl groups, etc. These functional groups will also react with a wide variety of other functional groups such as an aldehydo, isocyanato, acyl, diazo, azido, anhydro activated ester, etc., to produce covalent bonds. Nevertheless, this method also often has many disadvantages involving costly reactants and solvents, as well as specialized and costly porous supports and cumbersome multi-step procedures, which render the method of preparation uneconomical for commercial application.

The prior art is therefore replete with various methods for immobilizing enzymes. However, as will hereinafter be discussed in greater detail, none of the compositions involving the immobilization of enzymes will comprise the composition of matter of the present invention which constitutes a support system consisting of a treated monolayer of a carbonaceous pyropolymer possessing recurring units containing at least carbon and hydrogen atoms on a high surface area inorganic oxide, said support containing a copolymer, formed in situ from a polyfunctional monomer, a low molecular weight polymer, a polymer hydrolysate, or a preformed polymer of natural or synthetic origin by reaction with a bifunctional monomer which is entrapped and also adsorbed in part within the pores of said support, and which contains terminally functionalized pendent groups extending therefrom, as well as an enzyme being covalently bound to the active moieties in the terminal reactive portions of the pendent groups, thus permitting the freedom of movement which will enable the enzyme to exercise maximum activity as well as maximum stability. The maximum stability and resistance to disruption is due in part to the inorganic-organic matrix which is produced by the physical-chemical and mechanical bond between the inorganic support and the organic polymer which has been prepared in situ in the pores of the support.

As examples of patents which teach various immobilized enyme composites, U.S. Pat. No. 3,556,945 relates to enzyme composites in which the enzyme is adsorbed directly to an inorganic carrier such as glass. U.S. Pat. No. 3,519,538 is concerned with enzyme composites in which the enzymes are chemically coupled by means of an intermediary silane coupling agent to an inorganic carrier. In similar fashion. U.S. Pat. No. 3,783,101 also utilizes an organosilane composite as a binding agent, the enzyme being covalently coupled to a glass carrier by means of an intermediate silane coupling agent, the silicon portion of the coupling agent being attached to the carrier while the organic portion of the coupling agent is coupled to the enzyme, the composition containing a metal oxide on the surface of the carrier disposed between the carrier and the silicon portion of the coupling agent. In U.S. Pat. No. 3,821,083 a water-insoluble polymer such as polyacrolein is deposited on an inorganic carrier and an enzyme is then covalently linked to the aldehyde groups of the polymer. However, according to most of the examples set forth in this patent, it is necessary to first hydrolyze the composite prior to the deposition of the enzyme on the polymer. Additionally, the product which is obtained by the method of this patent suffers a number of disadvantages in that it first requires either the deposition, or initially the formation, of the desired polymer in an organic medium followed by its deposition on the inorganic carrier with a subsequent cleanup operation involving distillation to remove the organic medium. In addition to this, in another method set forth in this reference, an additional hydrolytic reaction is required in order to release the aldehyde groups from the initial acetal configuration in which they occurred in the polymer. Inasmuch as these aldehyde moieties are attached directly to the backbone of the polymer, the enzyme is also held adjacent to the surface of the polymer inasmuch as it is separated from the surface of the polymer by only one carbon atom of the reacting aldehyde group and, therefore, the enzyme is obviously subjected to the physicochemical influences of the polymer as well as being relatively immobilized and inhibited from assuming its optimum configuration. Another patent, namely, U.S. Pat. No. 3,705,084 discloses a macroporous enzyme reactor in which an enzyme is adsorbed on the polymeric surface of a macroporous reactor core and thereafter is cross-linked in place. By cross-linking the enzymes on the polymeric surface after adsorption thereof, the enzyme is further immobilized in part and cannot act freely as in its native state as a catalyst. The cross-linkage of enzymes in effect links them together, thereby preventing a free movement of the enzyme and decreases the mobility of the enzyme which is a necessary prerequisite for maximum activity.

U.S. Pat. No. 3,654,003 discloses a water-soluble enzyme conjugate which is prepared from an organic watern-soluble support to which the enzyme is cross-linked and whose utility is limited only to cleaning compositions and pharmaceutical ointments. However, this enzyme composition also suffers from the disadvantages of the close proximity and interlocking of the enzyme and support, as well as the poor mechanical strength which is generally exhibited by enzyme conjugates based on organic polymeric supports.

U.S. Pat. No. 3,796,634 also discloses an immobilized biologically active enzyme which differs to a considerable degree from the immobilized enzyme conjugates of the present invention. The enzyme conjugate of patent consists of an inorganic support comprising colloidal particles possessing a particle size of from 50 to 20,000 Angstroms with a polyethyleneimine, the latter being cross-linked with glutaraldehyde to staple the cross-linked polymer so formed as a monolayer on the surface of the colloidal particles, followed by adsorption of the enzyme directly onto this monolayer. Following this, the enzyme which is adsorbed as a monolayer on the surface of the colloidal particles is then cross-linked with additional glutaraldehyde to other adsorbed enzyme molecules to prevent them from being readily desorbed while in use. There is no indication of any covalent binding between enzyme and polymer matrix as is present in the present invention. By the enzyme molecules being cross-linked together on the surface of the support, this conjugate, therefore, is subjected to deactivation by both the cross-linking reaction and by the electronic and steric effects of the surface, said enzyme possessing limited mobility. Inasmuch as the product of this patent is colloidal in nature, it also possesses a very limited utility for scale-up to commercial operation, since it cannot be used in a continuous flow system such as a packed column because it would either be carried along and out of the system in the flowing liquid stream or, if a restraining membrane should be employed, the particles would soon become packed against the barrier to form an impervious layer. In addition, such a colloidal product could not readily be utilized in a fluidized bed apparatus, thereby limiting the chief utility to a batch type reactor such as a stirred tank type reactor from which it would have to be separated by centrifugation upon each use cycle. In contrast to this, the immobilized enzyme conjugates of the present invention may be employed in a wide variety of batch or continuous type reactors and therefore are much more versatile with regard to their modes of application.

In addition, another reference, U.S. Pat. No. 3,959,080 relates to a carrier matrix for immobilizing biochemically effective substances. However, the matrix which is produced according to this reference constitutes the product derived from the reaction of an organic polymer containing cross-linkable acid hydrazide or acid azide groups with a bifunctional cross-linking agent such as glutaraldehyde. However, this matrix also suffers from the relatively poor mechanical stability and other deficiencies which are characteristic of organic enzyme supports as well as the relatively complex organic reactions employed in preparing such polymeric hydrazides, etc.

Another U.S. Pat. No. 4,229,536 describes a method for immobilizing enzymes by treating an inorganic porous support material with a first bifunctional monomer followed by contact of the treated support material with a second bifunctional monomer and binding an enzyme to the support matrix. Thereafter, the enzyme-matrix complex is then treated with an additional amount of the second bifunctional monomer and additional enzyme. Prior U.S. patents also teach enzyme electrodes as, for example, U.S. Pat. No. 4,321,123. This patent teaches a coenzyme immobilized electrode in which a coenzyme is bonded to an inorganic refractory oxide such as alumina, silica or zeolite. However, the electrode is prepared by covalently attaching a redox-active species to the surface of the oxide by means of a condensation agent which, however, is not carried over into the final product. Following this, an enzyme is complexed and cross-linked to the redox-active species.

Likewise, in U.S. Pat. No. 4,240,889, the outside surface of a semi-permeable membrane has an enzyme immobilized thereon. The inside surface of the membrane is placed against an electrode which is capable of detecting hydrogen peroxide. The electrode surface therefore is encased by a semipermeable membrane and cannot feasibly be coated with a polymeric amine such as that utilized in the present invention.

While preparation of the carbonaceous pyropolymer-coated support which is utilized to immobilize an enzyme to provide an electrode has been described in U.S. Pat. No. 3,651,386, it was totally unexpected that the material could be used as a support for immobilizing enzymatic material thereon and that new and unexpected results, as hereinafter set forth in greater detail, could be obtained by preparing and utilizing such a combination.

BRIEF SUMMARY OF THE INVENTION

This invention relates to novel compositions of matter comprising surface-modified electrodes. More specifically, the invention is concerned with surface-modified electrodes which are useful in electrochemical cells, said electrodes comprising an enzyme immobilized on a treated support in which said support consists of a monolayer of a carbonaceous pyropolymer possessing recurring units containing at least carbon and hydrogen atoms composited on a high surface area refractory inorganic oxide. In addition, the invention is also concerned with a process for preparing these surface-modified electrodes.

The treated support which is utilized for immobilizing an enzyme thereon comprises a composition of matter consisting of at least a monolayer of a carbonaceous pyropolymer possessing recurring units containing at least carbon and hydrogen atoms composited on a high surface area refractory inorganic oxide, the carbonaceous pyropolymer replicating the surface area of the macropore volume of said refractory inorganic oxide. The aforesaid support is treated by contacting said support with a bifunctional monomer or polymer, and particularly a polyamine, followed by contact with a bifunctional monomeric material possessing suitable reactive moieties. The result of the contact of the latter two materials will result in an organic copolymer which is formed in situ by the reaction of the two compounds. This organic copolymer material, which forms one component of the desired support, is entrapped and also adsorbed in part in the pores of the aforesaid support material, and is further provided with functionalized pendant groups extending from one extremity thereof, the functional moieties of said pendant group being located at the terminal portions thereof due to the use of a sufficient excess of the bifunctional monomer, and available for covalent attachment to the enzyme.

The desired surface-modified electrodes of the present invention may be utilized in biological fuel cells, especially for the anodic oxidation of readily available fuel sources. This is made possible through the covalent and intimate attachment of a redox active enzyme to the activated support. Upon attachment, and under the proper conditions, the material flow of electrons from substrate-to-enzyme-to electron acceptor is altered with the electrons now passing through a resistor of some sort, for example, a motor, before being transferred to an electron acceptor, for example, oxygen. In this manner, the system then acts as a fuel cell. By utilizing the novel composition of matter of the present invention, a useful electrical energy is produced and, in addition, an ordinary chemical or a renewable resource chemical is being used as a substrate to generate the aforesaid electrical energy while at the same time, generating other potentially useful compounds. For example, glucono-δ-lactone may be obtained from a readily available source such as glucose by utilizing immobilized glucose oxidase. This compound upon hydrolysis, produces gluconic acid which may be used in the preparation of pharmaceutical and food products, as a sequestrant, in cleaning and pickling metals, etc. Similarly, the use of immobilized methanol dehydrogenase is advantageous for converting methanol to formaldehyde and then to formate plus providing electrical energy, while formate dehydrogenase may then be used for converting the formate to carbon dioxide plus additional energy. As was previously mentioned, renewable resource chemicals may be utilized as fuel sources in combination with their corresponding oxidases or dehydrogenases. Some specific examples of these renewable resources comprise sugars such as glucose and xylose; amino acids such as glycine, methionine, lysine, tryptophan, phenylalanine, etc; alcohols such as ethanol, methanol, propanol, phenol, etc.

By utilizing these electrodes in biological fuel cells, it is possible to lower the activation energy of the reaction, thereby lowering any over-potential problems which may otherwise be present. The use of a given immobilized enzyme as an electrode will permit the activation energy to be lowered if the enzyme is intimately coupled to the support, thereby, as hereinbefore set forth, lowering the over-potential which, in turn, should result in a benefit in the form of a lower voltage necessary for a given amperage. The advantage of utilizing such a biological fuel cell in addition to the creation of electrical energy will also result in a high specificity for the creation of desired products.

As an example of the difference which is present between the process of this invention utilizing an immobilized enzyme such as glucose oxidase in an electrochemical reaction as opposed to a purely chemical reaction, it is to be noted that glucose oxidase has a redox active compound, flavin adenine dinucleotide (FAD) as its prosthetic group. When part of the glucose oxidase molecule, the FAD can be reduced by glucose to form FADH$_2$ and these reducing equivalents are normally transferred to molecular oxygen to form H$_2$O$_2$. In a chemical reaction, these may be diagrammatically illustrated as follows:

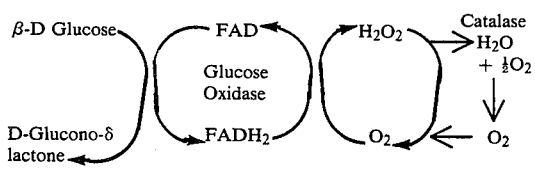

The requirement for oxygen to effect this reaction thus makes glucose oxidase an aerobic enzyme. Furthermore, the hydrogen peroxide which is formed may be detoxified by the enzyme catalase. In many instances where a similar system is used as an analytical device for the measurement of glucose concentrations, the actual species which is being measured is the hydrogen peroxide rather than the glucose.

In contradistinction to this, the system which is present when utilizing an immobilized enzyme of the present invention is substantially different from the chemical reaction just described. In the present process, the electrode system is now run anaerobically, with the result that rather than transferring electrons from the FADH$_2$ to oxygen, which occurred in the former system, electrons are transferred through the electrode of the electrochemical cell. Diagrammatically, this may be illustrated as follows:

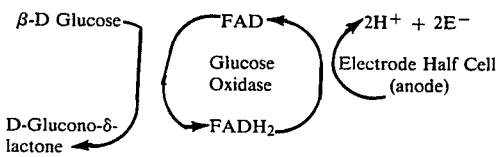

The advantages which are present when employing this system are that the electrons are transferred directly to the electrode composite, which in the present invention comprises an enzyme immobilized on a support comprising a carbonaceous pyropolymer possessing recurring units containing at least carbon and hydrogen atoms on a refractory inorganic oxide which has been treated to provide pendant groups for covalently binding the enzyme thereon, rather than to oxygen. Thus, no hydrogen peroxide is produced and, inasmuch as it is well known that hydrogen peroxide deactivates the glucose oxidase enzyme, will result in the advantage of a longer operating life for the electrochemical cell.

It is therefore an object of this invention to provide a novel composition of matter comprising a surface-modified electrode.

A further object of this invention is to provide a process for preparing surface-modified electrodes in which an enzyme is immobilized on a particular type of support hereinafter set forth in greater detail.

In one aspect an embodiment of this invention is found in a surface-modified electrode which comprises: (a) a refractory inorganic oxide having a surface area in the range of from about 1 to about 500 m$^2$/g and a macropore volume in the range of from about 50 to about 2000 Angstroms; (b) at least a monolayer of a carbonaceous pyropolymer possessing recurring units containing at least carbon and hydrogen atoms on said refractory inorganic oxide and having a surface area and macropore volume which replicates said surface area and macropore volume of said refractory inorganic oxide; (c) a layer of a polyamine polymer entrapped and adsorbed within the pores of said carbonaceous pyropolymer; (d) a bifunctional monomer in attachment with said polyamine polymer at one extremity and providing pendant terminal groups at the opposite extremity; and (e) an enzyme in conjugate attachment to said pendant terminal group.

Another embodiment of this invention is found in a method for the preparation of a surface-modified electrode which comprises; (a) forming a monolayer of a carbonaceous pyropolymer possessing recurring units containing at least carbon and hydrogen atoms on a refractory inorganic oxide support having a surface area in the range of from about 1 to about 500 m$^2$/g and a macropore volume in the range of from about 50 to about 2000 Angstroms, wherein said pyropolymer replicates said surface area and macropore size of said refractory inorganic oxide; (b) contacting said layer of pyropolymer with a solution of a water-soluble polyamine to entrap and adsorb said polyamine within the pores of said pyropolymer; (c) contacting said pyropolymeric layer with said polyamine entrapped and adsorbed therein with a molar excess of a bifunctional monomeric material to attach one extremity of said monomeric material to said polyamine and to provide pendant groups at the other extremity of said monomeric material; (d) contacting said pendant groups with an excess of an enzyme to form a conjugate attachment of said enzyme to said monomeric material and thereby to said carbonaceous pyropolymer-coated refractory inorganic oxide support; and (e) recovering the resultant surface-modified electrode.

A specific embodiment of this invention resides in a surface-modified electrode comprising glucose oxidase imnobilized on a treated support consisting of at least a monolayer of a carbonaceous pyropolymer possessing recurring units containing at least carbon and hydrogen atoms on a gamma-alumina possessing a surface area in the range from about 1 to about 500 $m^2/g$ and a macropore volume in the range of from about 50 to about 2,000 Angstroms.

Another specific embodiment of this invention resides in a method for the preparation of a surface-modified electrode which comprises treating a support consisting of at least one monolayer of a carbonaceous pyropolymer possessing recurring units containing at least carbon and hydrogen atoms on a gamma-alumina possessing a surface area in the range from about 1 to about 500 $m^2/g$ and a macropore volume in the range of from about 50 to about 2,000 Angstroms with a solution of diethylenetriamine, removing unabsorbed diethylenetriamine after said treatment, contacting said support with a solution containing a molar excess of glutaraldehyde to provide pendent bonding sites for enzymatic conjugate attachment thereto, removing unreacted glutaraldehyde, contacting the resultant treated support with glucose oxidase to effect conjugate attachment of said glucose oxidase to said support, and recovering the resultant surface-modified electrode.

Another specific embodiment of this invention is found in a process for generating useful electrical energy utilizing glucose as an oxidizable substrate in a fuel cell containing, as a surface-modified electrode, glucose oxidase immobilized on a treated support comprising at least a monolayer of a carbonaceous pyropolymer possessing recurring units containing at least carbon and hydrogen atoms composited on a high surface area gamma alumina, said support having been treated with triethylenediamine and gluteraldehyde prior to covalently attaching said glucose oxidase to said support.

Other objects and embodiments will be found in the following further detailed description of the present invention.

DETAILED DESCRIPTION OF THE INVENTION

As hereinbefore set forth, the present invention is concerned with surface-modified electrodes which may be used in biological fuel cells, said electrode comprising an enzyme which has been immobilized on a treated support to provide a covalent bonding of the enzyme to the support, said support consisting of at least a monolayer of a carbonaceous pyropolymer possessing recurring units containing at least carbon and hydrogen atoms on a high surface area refractory inorganic oxide. The carbonaceous pyropolymer which is composited on the refractory inorganic oxide will replicate the surface area and the macropore volume of the inorganic oxide and thus provide a surface in which an organic copolymer of the type hereinafter set forth in greater detail may be adsorbed and entrapped within the replicated pores to provide an attachment to said support. By utilizing a support comprising the carbonaceous pyropolymer composited on an inorganic refractory oxide to which an enzyme is immobilized, it is possible to utilize the resulting composition of matter as an electrode involved in the conversion of certain food materials. For example, when utilizing some inorganic oxides as a support per se for immobilizing an enzyme, it is possible that some undesirable factors may be introduced into the system. This may occur inasmuch as the refractory inorganic oxides may contain impurities such as oxides of heavy metals in the support which would render the use thereof impractical. The presence of the carbonaceous pyropolymer on the surface of the refractory inorganic oxide will prevent the dissolution of these impurities into the feed line or substrate and thus enable the immobilized enzyme to be utilized for a longer period of time due to the nonpoisoning thereof as well as preventing the introduction of the heavy metal oxides into the food system.

The support upon which the enzyme is immobilized after a treatment of said support in a manner hereinafter set forth in greater detail, comprises a high surface area refractory inorganic oxide such as alumina including gamma-alumina, eta-alumina, theta-alumina, etc., silica or mixtures of refractory inorganic oxides such as alumina-silica, etc. These refractory inorganic oxides are treated with a pyrolyzable organic compound. The refractory inorganic oxides which form the basis of the support will possess a surface area in the range of from about 1 to about 500 $m^2/g$ as well as possessing a macropore volume in the range of from about 50 to about 2,000 Angstroms and preferably a macropore volume in the range of from about 300 to about 1,500 Angstroms. The treatment of this inorganic oxide is effected at temperature conditions which are sufficient to pyrolyze a pyropolymer precursor to form a carbonaceous pyropolymer containing at least carbon and hydrogen atoms in recurring units. In one method of preparing the composite, the refractory inorganic oxide is heated to a temperature of from about 500° to about 1200° C. in a reducing atmosphere containing an organic pyrolyzable compound. The organic pyropolymer precursors most commonly and preferably used for the purposes of this invention are members of the group consisting of aliphatic oxygen derivatives, aliphatic sulfur derivatives, aliphatic nitrogen derivatives, organometallic compounds, alicyclic compounds, aromatic compounds and heterocyclic compounds. Of the aliphatic hydrocarbons, the more common classes which may be utilized to perform this invention are alkanes, alkenes, alkynes, and alkadienes. Ethane, propane, butane and pentane are among the alkanes which may be successfully used in the performance of this invention. Similarly, alkenes which suffice include ethene, propene, 1-butene, 2-butene, and 1-pentene. Alkynes which may be successfully used include ethyne, propyne, 1-butyne, 2-butyne, 1-pentyne, and 1-hexyne. 1,3-Butadiene and isoprene are included among the alkadienes which may be utilized. Among the aliphatic halogen derivatives which suffice for the purposes of this invention are monohaloalkanes, polyhaloalkanes, and unsaturated halo compounds. In the monohaloalkane subgroup, chloromethane, bromoethane, 1-iodopropane, and 1-chlorobutane may be used. Polyhaloalkanes such as carbon tetrachloride, chloroform, 1,2-dichloroethane, and 1,2- dichlorobutane may also be utilized. One unsaturated halo compound which nay be utilized is chloroprene.

The aliphatic oxygen derivatives appropriate for use in this invention include the classes of alcohols, ethers, halohydrides and alkene oxides, saturated aldehydes and ketones, unsaturated aldehydes and ketones, ketenes, acids, esters, salts and carbohydrates. Various alcohols which may be utilized include ethanol, 2-butanol, 1-propanol, glycol, (e.g. 1,3-propanediol), and glycerol. Ethers utilized include ethyl ether and isopropyl ether. Appropriate halohydrins and alkene oxides include ethylene chlorohydrin, propylene chlorohydrin, ethylene oxide, and propylene oxide. Suitable saturated aldehydes and ketones include formaldehyde, acetaldehyde, acetone, and ethyl methyl ketone. Unsaturated aldehydes and ketones which may be used include propenol, trans-2-butenal, and butenone. Ketene has also been successfully used as an organic pyrolyzable substance. Likewise, formic acid, acetic acid, oxalic acid, acrylic acid, chloroethanoic acid, formic anhydride and formyl chloride may also be utilized. Esters such as methyl formate, ethyl formate, and ethyl acetate may also be used. Salts such as sodium formate, potassium acetate, and calcium propionate may be utilized as may a variety of carbohydrates. The broad classification of aliphatic sulfur derivatives may be broken down into the subclasses of alkanethiols, alkylthioalkanes, sulfonic acids, and alkyl sulfates and alkyl metallic sulfates. Suitable among the alkanethiols are ethyl mercaptan and n-propyl mercaptan. Among the alkylthioalkanes usable are the thioethers, alkyl sulfides, methyl sulfide, ethyl sulfide, and methyl propyl sulfide. Ethyl sulfonic acid and n-propyl sulfonic acid are sulfonic acids which may also be successfully used. Ethyl sulfate and sodium laurel sulfate are also appropriate for use.

The broad class of aliphatic nitrogen derivatives may be broken down into the subclasses of nitroalkanes, amides, amines, nitriles, and carbylamines. Nitroethane and 1-nitropropane are exemplary of suitable nitroalkanes, while acetamide and propionamide are among the appropriate amides. Amines such as dimethylamine and ethylmethylamine, nitriles such as acetonitrile and propionitrile, and carbylamines such as ethylisocyanid may also be used for the organic pyrolyzable substance of this invention. Organometallic compounds such as tetraisopropyl titanate, tetrabutyl titanate, and 2-ethylhexyl titanate may also be used.

Particularly appropriate and preferred for use as the organo-pyrolyzable substance of this invention are the alicyclic compounds. Foremost among these are cyclohexane and cyclohexene. Aromatic compounds including the subclasses of hydrocarbons, halogen compounds, oxygen derivatives, ethers, aldehydes, ketones, quinones, aromatic acids, aroaatic sulfur derivatives, and aromatic nitrogen compounds may also be utilized. Among the many suitable hydrocarbons, benzene, naphthalene, anthracene and toluene were successfully utilized. Benzyl chloride and benzal chloride are appropriate halogen compounds while phenol, o-cresol, benzyl alcohol and hydroquinone are among the suitable derivatives. Ethers such as anisole and phenetole and aldehydes, ketones, and quinones, such as benzaldehyde, acetophenone, benzophenone, benzoquinone, and anthraquinone may also be used. Aromatic acids such as benzoic acid, phenylacetic acid, and hydrocinnamic acid may be utilized while the aromatic sulfur derivative of benzenesulfonic acid will also serve successfully. The aromatic nitrogen compounds of nitrobenzene, 1-nitronaphthalene, aminobenzene and 2-amine toluene may also be successfully used as the organic pyrolyzable substance of this invention. Among the heterocyclic compounds, five member ring compounds such as furan, proline, coumarone, thionaphthene, indole, indigo and carbazole may be successfully utilized. Six member ring compounds such as pyran, coumarin and acridine may also be utilized.

As can be seen, an extremely wide latitude can be exercised in the selection of the organic pyrolyzable substance, since virtually any organic material that can be vaporized, decomposed and polymerized on the refractory oxide by heating will suffice.

In another embodiment, the composite may be prepared by impregnating the refractory inorganic oxide with a solution of a carbohydrate material such as dextrose, sucrose, fructose, starch, etc., and thereafter drying the impregnated support. After drying, the impregnated support is then subjected to pyrolysis temperatures in the range hereinbefore set forth whereby a carbonaceous pyropolymer similar in nature to those hereinbefore described is formed in at least a monolayer on the surface of the refractory inorganic oxide support.

It is also contemplated within the scope of this invention that the support may also contain a catalytic or conductive metal by impregnating the pyropolymer composite with a solution of said metal. The impregnation is effected by treating the composite with an aqueous or organic solution of the desired metal or, if so desired, a combination of metals in an amount sufficient to deposit at least one catalytically active metal on the surface of the carbonaceous pyropolymer in an amount ranging from about 0.5 to about 20% by weight. Examples of catalytically active or conductive metals which may be employed will include platinum, palladium, ruthenium, rhodium, osmium, iridium, rhenium, nickel, copper, silver, gold, etc. It is to be understood that the catalytically active or conductive metals are only representative of the type of metals which may be impregnated on the surface of the carbonaceous pyropolymer and that the present invention is not necessarily limited thereto.

As hereinbefore set forth, the solution which is utilized to impregnate the carbonaceous pyropolymeric-inorganic oxide support may be aqueous in nature, some specific examples of these aqueous solutions including chloroplatinic acid, chloroplatinous acid, bromoplatinic acid, sodium platinate, potassium platinate, lithium platinate, platinic chloride, platinous chloride, the corresponding palladium, rhenium, ruthenium, osmium and iridium compounds, nickel chloride, nickel perchlorate, nickel sulfate, cupric bromide, cupric chloride, the water-soluble silver and gold salts, etc. After impregnation of the composite, the solvent is removed by heat to a temperature in the range of from about 100° to about 400° C., the temperature being that which is sufficient to evaporate said solvent and leave the metal or mixtures of metals impregnated on the surface of the carbonaceous pyropolymer. Thereafter, the composite may be dried at an elevated temperature ranging from about 100° to about 200° C. for a period of time ranging from about 2 to about 6 hours or more. The final step in the preparation of the desired composite is then effected by subjecting the metal-impregnated carbonaceous pyropolymer-inorganic composite to a reducing step in the presence of a reducing atmosphere or medium such as hydrogen at elevated temperatures of from about 200° to about 600° C. for a period of time which may range from about 0.5 to about 4 hours or more whereby the metallic compound is reduced to the metal in the form of particles. The resulting metal-impregnated carbonaceous pyropolymer-inorganic refractory oxide composite will then contain the catalytically active or conductive metal or mixture of metals with metal loading in the range of from about 0.5 to about 20% by weight, the mean particle size of the metal being in a range of from about 10 to about 25 Angstroms or more.

As will hereinafter be shown in the examples at the end of the specification, the carbonaceous pyropolymer will replicate the surface area and the macropore volume of the refractory inorganic oxide support, thus enabling the organic copolymer which is produced during the treatment of the support prior to immobilization of the enzyme thereon to be adsorbed and entrapped within the pores of the support to provide a firm bonding of the copolymer to said support.

The configuration of the carbonaceous pyropolymer possessing recurring units containing at least carbon and hydrogen atoms on a high surface area inorganic oxide will vary, depending upon the particular type of support which is utilized. For example, the high surface area inorganic oxide upon which the carbonaceous pyropolymer is deposited may be in spherical form, particulate form, as a monolith which ray be coated with a porous inorganic oxide, a membrane, fibers alone or woven into a cloth, etc. The particular size may also vary over a wide range, again depending upon the particular type of support which is employed as well as upon the substrate and type of installation in which the immobilized enzyme conjugate is to be used. For example, if the support is in spherical form, the sphere may range in size from about 0.01 inch to about 0.25 inch in diameter, the preferred size ranging from about 1/32 inch to about ⅛ inch in diameter. When the support is in particulate form, the particle size may also range between about the same limits. In terms of U.S. standard mesh size, such particles may range from about 2.5 to about 100 mesh with about 10-40 mesh sizes preferred. Likewise, if the support is in the shape of fibers, the fiber may range from about 0.5 to about 20 microns in diameter. It is to be understood that the aforementioned types of support and configuration and size of the various supports are given merely for purposes of illustration and it is not intended that the present invention be necessarily limited thereto.

The composition of matter of the present invention may be prepared in a relatively simple manner. In one embodiment, the support comprising the monolayer of a carbonaceous pyropolymer possessing recurring units containing at least carbon and hydrogen on a high surface area inorganic oxide which has been prepared according to the manner hereinbefore set forth may be treated with a solution preferably aqueous in nature of a polyfunctional monomer, a low molecular weight polymer, a polymer hydrolysate, or a preformed polymer, following which the unadsorbed solution is removed by any means known in the art such as draining, etc. It is also contemplated that other inexpensive organic solvents such as acetone, methanol, tetrahydrofuran, etc., may also be used as the carrier for the aforementioned initially added polyfunctional monomers or polymers. Following the removal of the unadsorbed solution, the wet porous support is then contacted with a sufficiently large excess of a second bifunctional monomer of from about 3 to about 50 or more mole proportions, relative to the initial additive which reacts therewith to provide pendant groups extending from the resulting copolymer containing unreacted terminal functional moieties. The reactive groups of the bifunctional monomer are preferably separated by a chain containing from about 4 to about 10 carbon atoms, which also may be a cyclic as well as a straight chain. This second bifunctional monomer will also be added preferably in an aqueous solution, whereby the copolymer which is both entrapped and also adsorbed in part in the pores of the inorganic support will be formed and from which pendent groups of the second monomer will extend. These pendent groups will contain unreacted terminal functonal moieties due to the fact that a sufficient excess amount of the second bifunctional monomer was employed in treating the organic polymeric material originally adsorbed on the support. The unreacted functional moieties are then available for covalent binding to the enzyme, which is added to the resulting organic-inorganic matrix, again usually in an aqueous solution. After removal of the unreacted materials by conventional means such as by treating, washing, etc., the enzyme covalently bound to the pendent functionalized groups remains attached at the terminal portions thereof. It is therefore readily apparent that the entire immobilization procedure can be conducted in a simple and inexpensive manner, for example, in a column packed with the inorganic supports, utilizing an aqueous or inexpensive solvent media, the procedure being conducted over a temperature differential which may range from subambient (about 5° C.) up to elevated temperatures of about 60° C., and preferably at ambient (about 20°-25° C.) temperature, said procedure being effected by utilizing a minimum of operating steps and, in addition, permitting a ready recovery of the excess reactants, unbound enzyme and finished composition of matter, of which the former may be reused.

In describing the preparation of the organic-inorganic supports of this invention, we wish it understood that the terms "first" and "second" reactants are employed to clearly represent the operating procedure, but are not to be considered as limiting in nature. Thus, the sequence of addition of those reactants may be reversed if desired, particularly when the excess of the bifunctional monomer is in the lower part of the indicated range, although not necessarily with equivalent results.

The copolymeric materials which are formed in situ in such a manner so that the copolymeric material is both entrapped and also adsorbed in part in the pores of the carbonaceous pryopolymer of the type hereinbefore set forth may be produced according to the general methods hereinbefore described, that is, by first adsorbing a solution containing from about 2 to about 50% of a polyfunctional monomer, polymer hydrolysate, or a preformed polymer including low molecular weight forms thereof; these polymeric additives being synthetic or naturally-occurring in origin, and which are preferably soluble in water or other solvents which are inert to the reactions subsequently employed. As hereinbefore set forth, it is contemplated within the scope of this invention that a second bifunctional monomer is then added in similar manner in solution to form an organic-inorganic matrix by further reaction with the original polyfunctional additive adsorbed on the inorganic support to produce a copolymer which may also be cross-linked. As hereinbefore set forth, the second bifunctional monomer reactant is present in an excess as needed to produce pendent terminally functionalized groups in the range of from about 2 to about 50 moles or more of bifunctional monomer per mole of monomer, hydrolyzed polymer or preformed polymer adsorbed on the inorganic support. The amount of the first monomer, etc. which is adsorbed on the support will depend on many variables including the types of porous support, the pH of the solution in which it is dissolved, the concentration of the material which is present, as well as reaction parameters including temperature, pressure, etc. While the excess of the second bifunctional monomer may range from about 2 to about 50 moles or more per mole of the original additive, etc., it is usually satisfactory that the excess be in the range of from about 4 to about 25 moles of bifunctional monomer. The unreacted excess monomer may be readily recovered for reuse as well as the unadsorbed polymeric material originally added to the support.

The functional groups which are present on the bifunctional monomer will comprise well-known reactive moieties such as amino, hydroxyl, carboxyl, thiol, carbonyl, etc., moieties. As was also hereinbefore set forth, the reactive groups of the bifunctional compounds are preferably, but not necessarily, separated by chains containing from about 4 to about 10 carbon atoms. The reactive moieties are capable of covalently bonding with both the initial additives and subsequently, after washing out unreacted materials, with the enzyme which is to be added in a subsequent step, said enzyme being then covalently bound to the functional group at the terminal portion of the pendent chain. After addition of the enzyme to this composition, a relatively stable enzyme conjugate will be produced which possesses high activity and high stability. The unadsorbed enzyme can also be recovered for reuse.

Specific examples of polyfunctional monomers, low molecular weight polymers, polymer hydrolysates or preformed polymers which may be initially adsorbed on the inorganic support will include water-soluble polyamines such as ethylenediamine, diethylenetriamine, triethylenetetramine, tetraethylenepentamine, pentaethylenehexamine, hexamethylenediamine, polyethyleneimine, etc; water-insoluble but solvent or aqueous acid-soluble polyamines such as methylenedicyclohexylamine, methylenedianiline, etc., and natural and synthetic, partially hydrolyzed polymers and preformed polymers, soluble in either aqueous or solvent media, such as partially hydrolyzed Nylon, collagen, polyacrolein, polymaleic anhydride, alginic acid, casein hydrolysate gelatin, etc. Some specific examples of intermediate bifunctional monomeric materials which may be added to the above enumerated products in an excess in the range hereinbefore set forth to produce an organic-inorganic matrix and which possess the necessary characteristics hereinbefore set forth include compounds such as glutaraldehyde, benzoquinone, adipoyl chloride, sebacoyl chloride, toluenediisocyanate, hexamethylenediisocyanate, terephthalic diesters or acyl halides, etc. Due to the large excess of intermediary or spacer bifunctional monomeric molecules which are used, the polymeric matrix which is formed will contain pendent groups comprising the spacer molecules, said molecules extending from the matrix and having reactive moieties available at the terminal portions thereof which are capable of reacting with the binding of the enzyme to the spacer molecules via covalent bonds. Therefore, it is readily apparent that a suitable organic-inorganic matrix which is applicable in many situations will be formed with the support material by adsorbing any of the type of materials hereinbefore described which are known to the art and then treated with any bifunctional monomer molecule which is also known to the art and is suitably functionalized to react with the original additive, provided that a large enough excess of the bifunctional molecule is used to provide pendent groups which are capable of subsequently reacting with the enzyme which is desired to be immobilized. By utilizing these functional pendent groups as a binding site for the enzymes, it will permit the enzymes to have a greater mobility and thus permit the catalytic activity of the enzyme to remain at a high level for a relatively longer period of time than will be attained when the enzyme has been immobilized by any of the other methods such as entrapment in a gel lattice, adsorption on a solid surface or cross-linkage of the enzyme with adjacent enzyme molecules by means of bifunctional reagents, etc. Not all formulations, however, will produce equivalent results in terms of stability or activity.

Examples of enzymes which may be immobilized by a covalent bonding reaction and which contain an amino group capable of reacting with an aldehydic, isocyanato, acyl, ester, etc. moiety of the pendent group which is attached to a polymeric material entrapped and also adsorbed in part in the pores of a porous support material will include trypsin, papain, hexokinase, beta-galactosidase (lactase), ficin, bromelain, lactate dehydrogenase, glucoamylase, chymotrypsin, pronase, glucose isomerase, acylase, invertase, amylase, glucose oxidase, pepsin, rennin, protease, xylanase, cellulase, etc. In addition to the above enumerated enzymes, other enzymes which are utilized for electrochemical reactions will include the following oxidases and dehydrogenases, said list including the Enzymes Commission Numbers which are recommended by the Nomenclature Committee of the International Union of Biochemistry. Some representative examples of these enzymes include alcohol dehydrogenase 1.1.1.1, glycerol dehydrogenase 1.1.1.6, methanol dehydrogenase 1.1.9.98, lactate dehydrogenase 1.1.1.27, glucose dehydrogenase 1.1.1.47, 1-octenol dehydrogenase 1.1.1.73, formate dehydrogenase 1.2.1.2, aldehyde dehydrogenase 1.2.1.3, glucose oxidase 1.1.3.4, alcohol oxidase 1.1.3.13, L-amino acid oxidase 1.4.3.2, D-amino acid oxidase 1.4.3.3, etc. It is to be understood that any enzyme whose active site is not blocked, inactivated, etc. in the covalent bonding may be used, although not necessarily with equivalent results. While the aforementioned was centered about pendant groups which contained, as a functional moiety thereon, an aldehydic or isocyanato group, it is also contemplated within the scope of this invention that the pendent group may contain other functional moieties capable of reaction with carbonyl sulfhydryl or other moieties usually present in enzymes. However, the covalent bonding of enzymes containing these other moieties with other pendant groups may not necessarily be effected with equivalent results and may also involve appreciably greater costs in preparing intermediates. It is to be understood that the aforementioned listing of monomers, hydrolysates, polymers and enzymes are only representative of the various classes of compounds which may be employed, and that the present invention is not necessarily limited thereto.

The preparation of the compositions of matter of the present invention is preferably effected in a batch type operation as heretofore already described in detail, although it is also contemplated within the scope of this invention that the formation of the finished composition of matter may also be effected in a continuous manner of operation. When a continuous type operation is used, the quantity of the support comprising at least a monolayer of a carbonaceous pyropolymer possessing recurring units containing at least hydrogen and carbon atoms on a high surface area inorganic oxide is placed in an electrode column. The support material as hereinbefore set forth may be in any form desired such as powders, pellets, monoliths, etc. and is charged to the column after which a previously aqueous solution of, for example, a polyfunctional amine is contacted with the support until the latter is saturated with the amine solution and the excess is then drained. An intermediary spacer such as a reactive bifunctional monomer molecule such as glutaraldehyde is then contacted with the saturated support, said bifunctional molecule being present in an excess in the range of from about 2 to about 50 moles or more per mole of polyfunctional amine, as hereinbefore set forth. The formation of the copolymeric matrix is thus effected in an aqueous system, said reaction being effected during a period of time which may range from about 1 to about 10 hours or more in duration, but is usually of short duration. Following the completion of the desired residence time, the excess glutaraldehyde is removed by draining and washing out any water-soluble and unreacted materials, which in the case of a polyamine is preferably done with a buffer solution possessing a pH of about 4.

To form an immobilized enzyme conjugate, an aqueous solution of an enzyme of the type hereinbefore set forth in greater detail is contacted or recycled through the column, thereby effecting a covalent bonding of the enzyme to the terminal aldehydic groups of the functionalized pendent moieties which extend from the matrix. This occurs until there is no further covalent binding of the enzyme to the pendent molecules. The excess enzyme is recovered in the effluent after draining and washing the column, the column thus being ready for use in chemical reactions in which the catalytic effect of the enzyme is to take place. These procedures are, for the most part, conducted within the time, temperature and concentration parameters hereinbefore described in the batch type procedure and will result in comparable immobilized enzyme complexes. It is also contemplated within the scope of this invention that with suitable modifications of pH and temperature parameters which will be obvious to those skilled in the art, the process may be applied to a wide variety of inorganic porous supports, polymer-forming reactants and enzymes.

As hereinbefore set forth, the novel compositions of matter of the present invention may be utilized as a surface-modified electrode in electrochemical fuel cells. It is contemplated within the scope of this invention that the surface-modified electrode may be utilized in any type of electrochemical cell known in the art. As a representative example of the type of electrochemical cell which may be employed, the cell may be constructed of a nonconductive material such as glass, particularly pyrex glass. The dimensions of the cell are not of paramount importance, being dependent upon the type and size of the electrodes which are employed as well as other operating parameters. In one preferred embodiment, the cell will be cylindrical in configuration, the benefit accruing to this type of configuration being that there will be less edge effects due to the fact that the working electrode may be positioned equidistant from all inner surfaces of the cell and counter-electrode. The working electrode will comprise the composition of matter of the present invention, that is, an enzyme immobilized on a treated support comprised of at least a monolayer of a carbonaceous pyropolymer possessing recurring units containing at least carbon and hydrogen atoms composited on a high surface area inorganic oxide.

In one embodiment, the composition of matter is enclosed within a cylinder of a conductive metal such as platinum, palladium, copper, etc. which acts as a current collector while the packed composition of matter will act as the immobilized enzyme electrode. The counter-electrode is also composed of a conducting metal such as platinum, palladium, etc. In addition, the electrochemical cell will also contain a barrier which may, in some instances, act as a membrane to physically separate the two electrodes. This barrier may be formed of such material sold under the trade name of thirsty Vicor, which is a porous quartz, or from fritted glass, porous porcelain, etc. The barrier will possess relatively small pores, that is, pores which may have an average pore diameter of about 40 Angstroms with a void space of about 28% of its total volume, thus permitting the passage of charged ions between the electrodes, although larger pores may be desirable under certain circumstances. If so desired, although not necessary, the counter-electrode may be placed inside a tube of this material, said outer tube again acting as a barrier to separate the two electrodes. In addition, the cell will also be provided with wires leading to the working and counter-electrodes, the cell being provided with means for insuring an air-tight cell. It is to be understood that the above description of an electrochemical cell is only representative of the type of cell which may be employed and that the present invention is not necessarily limited thereto.

The aforementioned electrochemical cell containing as a working electrode an enzyme immobilized on a treated support of the type hereinbefore set forth in greater detail may be utilized for a wide variety of reactions, being used in analytical chemistry and the electron transport and in the co-factor regeneration for chemical synthesis. The type of substrates which are employed for the various chemical reactions will, of course, be dependent upon the particular reaction involved. Some specific examples of substrates which may be used in this electrochemical cell will include glucose, fructose, lactose, alcohols such as methanol, ethanol, propanol, etc., formic acid, L-amino acids, D-amino acids L-glutamine, L-tryosine, etc.

The following examples are given to illustrate the novel compositions of matter of the present invention, and a method for preparing these compositions as well as the use thereof in electrochemical cells. However, it is to be understood that these examples are given merely for purposes of illustration and that the present invention is not necessarily limited thereto.

EXAMPLE I

To illustrate the preparation of the novel composition of the present invention, a support was prepared by treating gammaalumina in the form of spheres which were ground to a range of from 25 to 35 U.S. mesh with benzene at a temperature of 900° C. in an inert atmosphere to form at least a monolayer of a carbonaceous pyropolymer possessing recurring units containing at least carbon and hydrogen atoms on the surface of the alumina. The alumina which was used for the support had a surface area of about 100 $m^2/g$ and a macropore volume in the range of from about 50 to about 2,000

Angstroms. Following the preparation of this support, 10.5 grams was added to 60 ml of an aqueous solution containing 1.5% polyethyleneimine. The impregnated support was placed in a vacuum and allowed to remain therein with occasional agitation for a period of 1 hour. The excess liquid was removed and the support was treated for a period of about 5 hours on a Buchner funnel. In order to insure further drying, the impregnated support was allowed to remain at room temperature for an additional period of 40 hours.

The imine-impregnated support was then treated with a solution of 4% benzoquinone dissolved in acetone using 4.0 ml for each ½ gram of the support. The treatment, which was effected at ambient temperature and pressure, was allowed to proceed for a period of approximately 1.5 hours, following which the treated support was washed with acetone and water to remove excess benzoquinone. The immobilization of the enzyme on the treated support was effected by contacting said support with a solution containing 1.5 ml of amyloglucosidase of 91 Miles Units per ml in a 30% solution of malto-dextrin 150 and 0.1% sodium benzoate which was neutralized to a pH of 4.3 with acetic acid. To test the activity of the immobilized enzyme composition of matter, the composition of matter was packed into a column and a solution of 30% malto-dextrin 150 containing 0.1% sodium benzoate as a preservative was flowed through the column at a flow rate of 10.8 ml per minute. The amount of glucose obtained by the reaction was found utilizing a Beckman glucose analyzer. The analysis determined that there was an activity of 31.8 Miles Units per gram, said Miles Units being the amount of enzyme which will catalyze the production of 1 gram of glucose in one hour at 60° C. The 31.8 Miles Units corresponds to 2945 International units per gram.

EXAMPLE II

In this example, a support, which was prepared in a manner similar to that hereinbefore set forth in Example I above, which was treated with polyethyleneimine and benzoquinone, was used as an immobilized enzyme support by treating the support with a solution containing 50 mg of glucose oxidase in 4 ml of a potassium phosphate which had a pH of 6.2. In order to assay for the quantity of active enzyme immobilized on the support, the resultant immobilized enzyme composition of matter was ground to particle size. A 15% glucose solution containing 0.1 molar potassium phosphate, pH 6.2, was saturated with oxygen and 3 ml of this glucose solution was placed in a Clark oxygen electrode chamber. Following this, 10 μl of a suspension of the ground-up immobilized glucose oxidase was added and the rate of oxygen consumption was measured. The rate of oxygen consumption is proportional to the rate of glucose consumption in a 1:1 ratio. Analysis of the product over a period of 1 minute showed the activity of the immobilized glucose oxidase to be 3,408 units, one unit equaling 1 micromole of oxygen consumed per minute at 25° C. The coupling efficiency (units of enzyme active in the immobilized state ÷ units of enzyme removed from the supernatant) was 21%.

EXAMPLE III

In this example, a support comprising at least a monolayer of a carbonaceous pyropolymer possessing recurring units of at least carbon and hydrogen atoms on a high surface area inorganic oxide which was prepared according to the method set forth in Example I was treated with polyethyleneimine and benzoquinone to form a treated support. After thoroughly washing the treated support to remove excess benzoquinone, glucose oxidase was immobilized thereon by impregnating the treated support with a solution containing 100 mg of glucose oxidase in 10 ml of a potassium phosphate solution which had a pH of 6.2. The immobilization was effected for a period of 1.5 days following which the resulting composition of matter comprising the immobilized glucose oxidase on the treated support was thoroughly washed to remove any unreacted glucose oxidase.

An electrochemical cell which comprised a counter-electrode of platinum and a working electrode of 4.7 grams of the immobilized glucose oxidase packed into a platinum mesh tube, the electrodes being separated by a thirsty Vicor barrier, was prepared. The substrate which was employed comprised a solution containing 15% glucose and 0.1 molar potassium phosphate. The scan of the electrochemical cell at 0.2 millivolts per second between −0.5 volts and +0.65 volts was compared to Ag/AgCl which has a specific potential and was used as the zero point for comparison. At 0.65 volts, a maximum amperage of about 22 milliamps was obtained.

EXAMPLE IV

A treated support was prepared by contacting an inorganic oxide support containing a monolayer of a carbonaceous pyropolymer possessing recurring units containing at least carbon and hydrogen atoms with polyethyleneimine and removing unreacted polyethyleneimine by washing. The resulting composite in an amount of 4.70 grams was contacted with 20 ml of a 3% benzoquinone in acetone solution. After allowing the reaction to proceed for a period of 1.5 hours, the desired treated support was washed thoroughly with acetone four times and then ten times with deionized water. The treated support was then impregnated using 200 mg of glucose oxidase in 10 ml of potassium phosphate, said immobilization being allowed to proceed for a period of 1.5 days with constant agitation. The immobilized enzyme composite was then washed to remove unreacted enzyme and placed in an electrochemical cell similar to that hereinbefore described. The working electrode comprised 7.5 mg of the immobilized enzyme, while the substrate was glucose which contained a buffer, raising the pH to 8.3. At a voltage of 0.05 as measured vs. the Ag/AgCl reference electrode, the amperage began to rise in a rapid fashion. At 0.65 volts, there was obtained an amperage of 150 milliamps which converted to 32 milliamps per gram of support.

EXAMPLE V

In this example, the experiment set forth in Example IV above was repeated, the only variant in this experiment being that the temperature of the electrochemical cell was controlled at 25° C. An amperage of 95 milliamps at 0.65 volts was obtained during this run.

EXAMPLE VI

To illustrate the fact that the carbonaceous pyropolymer possessing recurring units containing at least carbon and hydrogen atoms composited on a refractory inorganic oxide support substrate duplicates the surface area and macropore volume of the refractory inorganic oxide, measurements were performed in which a support was prepared in a manner similar to that set forth in Example I above, that is, gamma-alumina was treated with benzene at a temperature of about 900° C. to form the desired product. The results of these analyses are set forth in Table I below. In this Table, the gamma-alumina is labeled Support A, while the support containing at least a monolayer of a carbonaceous pyropolymer possessing recurring units containing at least carbon and hydrogen atoms composited on the surface of the alumina is labeled Support B.

TABLE I

|  | Support A | Support B |
|---|---|---|
| Macropore Volume cc/g (300–10,000 Angstroms) | 1.42 | 1.14 |
| Micropore Volume cc/g (300 Angstroms) | 0.35 | 0.151 |
| Maxima, Angstroms | 950,750,160,100 | 600,103,60 |
| Surface Area (m²/g) | 117 | 104 |

EXAMPLE VII

To illustrate the unexpected activity when utilizing an enzyme immobilized on the solid support of the present invention when compared with other electrodes, a series of experiments were performed. The experiments were performed in an electrochemical cell similar to that described in Example III above in which the electrodes were separated by a thirsty Vicor® barrier. The variables which were used in Test C included two platinum electrodes and a substrate comprising 0.1 M potassium phosphate having a pH of 6.2. Example D utilized, as the working electrode, a carbonaceous pyropolymer possessing recurring units containing at least carbon and hydrogen atoms composited on gamma-alumina as the working electrode plus a solution of the 0.1 M potassium phosphate. Experiment E utilized, as the working electrode, the composition of Experiment D and a substrate comprising a solution containing a 15% glucose plus the potassium phosphate. Experiment F utilized as the working electrode, glucose oxidase immobilized on the carbonaceous pyropolymer-coated gamma-alumina which was prepared according to the process of the present invention, the substrate comprising a solution containing 15% glucose plus the potasssium phosphate. Experiment G utilized a working electrode comprising the immobilized glucose oxidase on the carbonaceous pyropolymer-coated gamma-alumina, in a solution containing 0.1 molar potassium phosphate. A silver/silver chloride was used as a reference while performing the experiments at a temperature of 30° C. The results of these experiments are set forth in Table II below:

TABLE II

| Applied Potential vs. Ag/AgCl | C | D | E | F | G |
|---|---|---|---|---|---|
| Reducing |  |  |  |  |  |
| −0.45 | −0.0057 | −0.99 | −1.78 | −4.02 | −2.68 |
| −0.35 | −0.0037 | −0.16 | −0.43 | −0.97 | −1.97 |
| −0.25 | −0.0033 | +0.37 | −0.26 | −0.15 | −0.15 |
| −0.15 | −0.0024 | +0.58 | +0.35 | +0.46 | +0.45 |
| −0.05 | −0.0016 | +0.48 | +0.43 | +0.97 | +0.49 |
| 0 | −0.0013 | +0.46 | — | — | — |
| Oxidizing |  |  |  |  |  |
| +0.05 | +0.0009 | +0.50 | +0.59 | +1.37 | +0.58 |
| +0.15 | +0.0003 | +0.57 | +0.54 | +1.94 | +0.74 |
| +0.25 | +0.0003 | +0.64 | +0.84 | +2.75 | +0.98 |
| +0.35 | +0.0023 | +0.94 | +1.13 | +3.86 | +1.31 |
| +0.45 | +0.0056 | +1.12 | +1.20 | +5.33 | +1.42 |
| +0.55 | +0.0054 | +1.38 | +1.84 | +6.95 | +2.40 |
| +0.65 | +0.0071 | +1.85 | +2.45 | +8.53 | +3.82 |

TABLE II-continued

| Applied Potential vs. Ag/AgCl | C | D | E | F | G |
|---|---|---|---|---|---|
|  |  | After 16 H |  |  |  |
|  |  | 0.49 | 0.83 | 1.86 | 1.17 |

It will be readily observable from the above Table that the working electrode which comprised glucose oxidase immobilized on a support comprising a treated carbonaceous pyropolymer possessing recurring units containing at least carbon and hydrogen atoms composited on gamma-alumina resulted in a much greater current than other systems which did not provide this type of working electrode.

EXAMPLE VIII

Other surface-modified electrodes may be prepared in a similar manner by treating a support comprising at least a monolayer of a carbonaceous pyropolymer possessing recurring units containing at least carbon and hydrogen atoms on a high surface area inorganic oxide with a polyamine such as triethylenetetramine, removing unreacted amine and forming a polymer by treatment of the impregnated inorganic oxide with glutaraldehyde. After removal of the unreacted glutaraldehyde by a thorough washing, the treated support may have enzymes such as glucose dehydrogenase, methanol oxidase, methanol dehydrogenase, and formate dehydrogenase immobilized thereon by impregnation of the support with a solution of the particular enzyme. The resultant immobilized enzymes may then be used as working electrodes in an electrochemical cell using various substrates such as glucose, methyl alcohol, formate, etc. and an electric current may be generated in the cell.

We claim as our invention:

1. A surface-modified electrode which comprises:
   (a) a refractory inorganic oxide having a surface area in the range of from about 1 to about 500 m²/g and a macropore volume in the range of from about 50 to about 2000 Angstroms;
   (b) at least a monolayer coating of a carbonaceous pyropolymer possessing recurring units containing at least carbon and hydrogen atoms on said refractory inorganic oxide and said monolayer coating replicating the surface area and macropore volume of said refractory inorganic oxide;
   (c) a layer of a polyamine polymer entrapped and adsorbed within the pores of said carbonaceous pyropolymer;
   (d) a bifunctional monomer in attachment with said polyamine polymer at one extremity and providing pendant terminal groups at the opposite extremity; and
   (e) an enzyme in conjugate attachment to said pendant terminal groups.

2. The surface-modified electrode as set forth in claim 1 in which said refractory inorganic oxide is an alumina.

3. The surface-modified electrode as set forth in claim 2 in which said alumina is gamma-alumina.

4. The surface-modified electrode as set forth in claim 1 in which said enzyme is glucose oxidase.

5. The surface-modified electrode as set forth in claim 1 in which said enzyme is glucose dehydrogenase.

6. The surface-modified electrode as set forth in claim 1 in which said enzyme is methanol oxidase.

7. The surface-modified electrode as set forth in claim 1 in which said enzyme is methanol dehydrogenase.

8. The surface-modified electrode as set forth in claim 1 in which said enzyme is formate dehydrogenase.

9. The surface-modified electrode as set forth in claim 1 in which said layer of a carbonaceous pyropolymer contains a catalytic or conductive material.

10. The surface-modified electrode as set forth in claim 9 in which said catalytic or conductive metal is platinum.

11. The surface-modified electrode as set forth in claim 9 in which said catalytic or conductive metal is palladium.

12. A method for the preparation of a surface-modified electrode which comprises:
(a) forming a monolayer coating of a carbonaceous pyropolymer possessing recurring units containing at least carbon and hydrogen atoms on a refractory inorganic oxide support having a surface area in the range of from about 1 to about 500 m²/g and a macropore volume in the range of from about 50 to about 2000 Angstroms, wherein said pyropolymer coating replicates said surface area and macropore size of said refractory inorganic oxide;
(b) contacting said layer of pyropolymer with a solution of a water-soluble polyamine to entrap and adsorb said polyamine within the pores of said pyropolymer;
(c) contacting said pyropolymeric layer with said polyamine entrapped and adsorbed therein with a molar excess of a bifunctional monomeric material to attach one extremity of said monomeric material to said polyamine and to provide pendant groups at the other extremity of said monomeric material;
(d) contacting said pendant groups with an excess of an enzyme to form a conjugate attachment of said enzyme to said monomeric material and thereby to said carbonaceous pyropolymer-coated refractory inorganic oxide support; and
(e) recovering the resultant surface-modified electrode.

13. The method as set forth in claim 12 in which said refractory inorganic oxide is gamma-alumina.

14. The method as set forth in claim 12 in which said polyamine is ethylenediamine.

15. The method as set forth in claim 12 in which said polyamine is diethylenediamine.

16. The method as set forth in claim 12 in which said monomeric material is glutaraldehyde.

17. The method as set forth in claim 12 in which said monomeric material is benzoquinone.

18. The method as set forth in claim 12 in which said enzyme is glucose oxidase.

19. The method as set forth in claim 12 in which said enzyme is methanol dehydrogenase.

20. The method as set forth in claim 12 in which said carbonaceous pyropolymer support contains a catalytic or conductive metal.

21. The method as set forth in claim 20 in which said metal is platinum.

22. The method as set forth in claim 20 in which said metal is palladium.

* * * * *